(12) United States Patent
Lee et al.

(10) Patent No.: US 11,660,588 B2
(45) Date of Patent: May 30, 2023

(54) CATALYST FOR PRODUCING C8 AROMATIC HYDROCARBON HAVING REDUCED ETHYLBENZENE CONTENT AND PREPARATION METHOD THEREFOR

(71) Applicant: SK Innovation Co., Ltd., Seoul (KR)

(72) Inventors: Sang Il Lee, Daejeon (KR); Ji Hoon Lee, Daejeon (KR); Young Eun Cheon, Daejeon (KR); Yeon Ho Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 113 days.

(21) Appl. No.: 17/083,629

(22) Filed: Oct. 29, 2020

(65) Prior Publication Data

US 2021/0129122 A1 May 6, 2021

(30) Foreign Application Priority Data

Oct. 30, 2019 (KR) .................. 10-2019-0136059

(51) Int. Cl.

| | | |
|---|---|---|
| C07C 2/66 | (2006.01) |
| B01J 29/80 | (2006.01) |
| B01J 21/04 | (2006.01) |
| B01J 23/62 | (2006.01) |
| B01J 27/045 | (2006.01) |
| B01J 27/051 | (2006.01) |
| B01J 29/22 | (2006.01) |
| B01J 29/26 | (2006.01) |
| B01J 29/44 | (2006.01) |
| B01J 29/48 | (2006.01) |
| B01J 29/78 | (2006.01) |
| B01J 37/00 | (2006.01) |
| B01J 37/04 | (2006.01) |
| B01J 37/16 | (2006.01) |
| B01J 37/20 | (2006.01) |
| B01J 37/30 | (2006.01) |
| C07C 4/18 | (2006.01) |
| C07C 6/12 | (2006.01) |
| C07C 5/22 | (2006.01) |
| C07C 4/06 | (2006.01) |
| C07C 15/08 | (2006.01) |
| C10G 35/095 | (2006.01) |
| B01J 29/06 | (2006.01) |

(52) U.S. Cl.
CPC .............. *B01J 29/80* (2013.01); *B01J 21/04* (2013.01); *B01J 23/626* (2013.01); *B01J 27/045* (2013.01); *B01J 27/0515* (2013.01); *B01J 29/22* (2013.01); *B01J 29/26* (2013.01); *B01J 29/44* (2013.01); *B01J 29/48* (2013.01); *B01J 29/7815* (2013.01); *B01J 37/0018* (2013.01); *B01J 37/04* (2013.01); *B01J 37/16* (2013.01); *B01J 37/20* (2013.01); *B01J 37/30* (2013.01); *C07C 2/66* (2013.01); *C07C 4/06* (2013.01); *C07C 4/18* (2013.01); *C07C 5/222* (2013.01); *C07C 6/123* (2013.01); *C07C 6/126* (2013.01); *C07C 15/08* (2013.01); *C10G 35/095* (2013.01); *B01J 2029/062* (2013.01); *B01J 2229/186* (2013.01); *C07C 2521/04* (2013.01); *C07C 2523/28* (2013.01); *C07C 2523/36* (2013.01); *C07C 2523/42* (2013.01); *C07C 2523/62* (2013.01); *C07C 2529/18* (2013.01); *C07C 2529/22* (2013.01); *C07C 2529/26* (2013.01); *C07C 2529/44* (2013.01); *C07C 2529/74* (2013.01); *C07C 2529/78* (2013.01); *C07C 2529/80* (2013.01); *C10G 2400/30* (2013.01); *Y02P 20/52* (2015.11)

(58) Field of Classification Search
CPC .......... C07C 6/26; C07C 6/123; C07C 6/126; C07C 4/06; C07C 4/18; C07C 2/66; C07C 5/222; C07C 15/08; C07C 2521/04; C07C 2523/28; C07C 2523/36; C07C 2523/42; C07C 2529/80; C07C 2529/74; C07C 2529/44; C07C 2529/26; C07C 2529/22; C07C 2529/78; C07C 2529/18; C07C 2523/62; Y02P 20/52; C10G 35/095; C10G 2400/30
USPC ........ 585/470, 475, 483, 486, 485, 488, 489
See application file for complete search history.

(56) References Cited

U.S. PATENT DOCUMENTS

| | | |
|---|---|---|
| 3,140,249 A | 7/1964 | Plank et al. |
| 3,140,251 A | 7/1964 | Plank et al. |
| 5,759,950 A | 6/1998 | Gui et al. |
| 7,314,601 B2 | 1/2008 | Negiz et al. |
| 8,481,795 B2 | 7/2013 | Boldingh et al. |
| 2005/0234279 A1 | 10/2005 | Serra et al. |
| 2009/0093661 A1 | 4/2009 | Guillon et al. |

(Continued)

FOREIGN PATENT DOCUMENTS

| | | |
|---|---|---|
| CN | 101190866 A | 6/2008 |
| DE | 102007005703 A1 | 4/2008 |

(Continued)

OTHER PUBLICATIONS

Machine translation of CN 101190866 A, Jun. 4, 2008.*

*Primary Examiner* — Elizabeth D Wood
(74) *Attorney, Agent, or Firm* — The Webb Law Firm

(57) ABSTRACT

Disclosed are a catalyst and a preparation method therefor, the catalyst being able to maintain a high production yield of C8 aromatic hydrocarbons in the process of converting a feedstock containing alkyl aromatics to C8 aromatic hydrocarbons such as mixed xylene through disproportionation/transalkylation/dealkylation while reducing a content of ethylbenzene in the products.

15 Claims, 1 Drawing Sheet

(56) References Cited

U.S. PATENT DOCUMENTS

2012/0065446 A1 3/2012 Boldingh
2019/0284110 A1 9/2019 Canos et al.

FOREIGN PATENT DOCUMENTS

RU 2108863 C1 4/1998
WO 2007120951 A3 10/2007

* cited by examiner

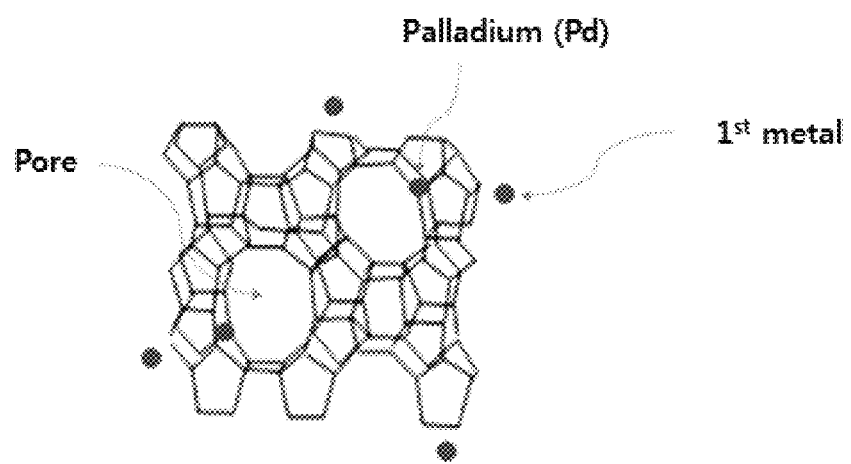

CATALYST FOR PRODUCING C8 AROMATIC HYDROCARBON HAVING REDUCED ETHYLBENZENE CONTENT AND PREPARATION METHOD THEREFOR

CROSS-REFERENCE TO RELATED APPLICATION

This application claims priority to Korean Patent Application No. 10-2019-0136059 filed Oct. 30, 2019, the disclosure of which is hereby incorporated by reference in its entirety.

BACKGROUND OF THE INVENTION

1. Field of the Invention

The present disclosure relates to a catalyst for producing C8 aromatic hydrocarbons having a reduced ethylbenzene content and a preparation method therefor. More particularly, the present disclosure relates to a catalyst which is useful for converting a feedstock containing alkyl aromatic hydrocarbons to C8 aromatic hydrocarbons such as mixed xylenes through disproportion/transalkylation/dealkylation, whereby the C8 aromatic hydrocarbons can be produced at high yield, while reducing ethylbenzene content therein, and a preparation method therefor.

2. Description of the Prior Art

C8 aromatic hydrocarbons, particularly, mixed xylenes (or xylene isomers) account for a large portion of sources for basic chemicals in the petrochemical field. Mixed xylenes typically include meta-xylene (m-xylene), para-xylene (p-xylene), and ortho-xylene (o-xylene). Among them, p-xylene is a raw material for the synthesis of terephthalic acid that is used for manufacturing synthetic fabric fibers and resins and o-xylene serves as a raw material for the production of phthalic anhydride. On the other hand, m-xylene is used in plasticizers, azo dyes, etc. Similar boiling points among the xylene isomers make it difficult to separate particular xylenes from mixed xylenes by typical distillation. Instead, adsorption separation, crystallization, and isomerization are mainly employed for the separation and recovery of individual xylenes.

Largely, commercial preparation of mixed xylenes is achieved by separation and recovery from mixed xylene-rich fractions or by synthesis through reactions.

Representative of the former are a method in which mixed xylenes are separated through distillation of reformates obtained by catalytic reforming of naphtha and a method in which mixed xylenes are separated from pyrolysis oil generated as byproducts upon thermal cracking of naphtha. However, the mixed xylene-rich fractions obtained by catalytic reforming or thermal cracking are not composed of isomers at ratios suitable for meeting the market demand. The latter is generally accompanied with reactions in which aromatic hydrocarbons are converted to xylene in the presence of a catalyst, which is typically capable of disproportionation of toluene, transalkylation of toluene/C9+ aromatic compounds, dealkylation of C9+ alkyl aromatic compounds, and/or alkylation of toluene by methanol. However, the C8 aromatic hydrocarbons (mixed xylene) prepared by such methods may contain ethylbenzene. Ethylbenzene is recirculated to p-xylene recovery units, and decreases the efficiencies of p-xylene separation processes (e.g., PAREX process), thus increasing the total process cost.

In recent years, there has been a growing interest in the use of zeolite-based catalysts for converting aromatic hydrocarbons (aromatic hydrocarbons including benzene, toluene, and/or C9+ aromatics) to C8 aromatic hydrocarbons because only limited amounts of xylene can be produced by the conventional processes such as catalytic reforming. In this regard, it is advantageous to increase recovery yield of mixed xylene by reducing the content of ethylbenzene in the product. Generally, the C8 aromatic products vary in ethylbenzene content, depending on various factors including catalyst, reaction condition, and so on. As such, olefins such as ethylene, propylene, etc. are preferably removed by hydrogenation as fast as possible when they are generated by the dealkylation in the conversion process. The reason is not only because olefins are re-alkylated to aromatic compounds, resulting in the reduced conversion of C9+ aromatic compounds, but also because olefins themselves induce polymerization or aromatization to promote the formation of coke, which leads to deactivation of the catalysts, and to the increased amount of ethylbenzene in the C8 aromatic hydrocarbons.

Under these circumstances, various transalkylation catalysts having hydrogenation metals (e.g., noble metal such as platinum, etc. or base metals, such as molybdenum, etc.) supported on zeolite have been developed (for example, U.S. Pat. No. 8,481,795, and WO2007/120951 A1). Such conventional techniques can reduce contents of ethylbenzene to some degree, but are limited in improving catalyst durability and decreasing ethylbenzene contents in C8 aromatic hydrocarbons.

SUMMARY OF THE INVENTION

In an illustrative embodiment, the present disclosure provides a catalyst suitable for use in producing C8 aromatic hydrocarbons having a reduced ethylbenzene content, and a preparation method therefor.

In another illustrative embodiment, the present disclosure provides a process capable of producing mixed xylene at high yield from a feedstock containing an alkyl aromatic by using the catalyst having an improved property.

A first aspect of the present disclosure provides a catalyst comprising:

(A) a mixed support comprising (i) an MFI-type first zeolite having a silica-alumina ratio (SAR) of 10 to 200 and containing a reduced form of palladium (Pd) inside the pores thereof, and (ii) a second zeolite having a silica-alumina ratio of 10 to 200 and a pore size of 6 to 9 Å; and (B) at least one first metal supported onto the mixed support and selected from the group consisting of platinum (Pt), rhenium (Re), and molybdenum (Mo);

wherein the first metal is used in an amount of 0.01 to 5% by weight, based on the total weight of the catalyst.

According to an exemplary embodiment, the first zeolite may contain palladium at a content of 0.001 to 0.25% by weight, based on the weight thereof.

According to an exemplary embodiment, the first metal may be in a reduced form, a partially oxidized form, or a sulfide form.

According to an exemplary embodiment, the catalyst may further comprise a second metal selected from the group consisting of tin (Sn), lead (Pb), and a combination thereof, wherein the second metal is used in an amount of 0.01 to 5% by weight, based on the total weight of the catalyst.

According to an exemplary embodiment, the atomic ratio of the first metal to the second metal may be in the range of 1:0.5 to 50.

According to an exemplary embodiment, the first metal may be in a reduced form or in a partially reduced oxide form.

According to an exemplary embodiment, the mixed support may comprise: (i) 5 to 70% by weight of the first zeolite, (ii) 10 to 90% by weight of the second zeolite, and (iii) 1 to 70% by weight of an inorganic binder, based on the weight thereof.

According to an exemplary embodiment, the inorganic binder may be at least one selected from the group consisting of gamma-alumina, silica, silica-alumina, bentonite, kaolin, clinoptilolite, and montmorillonite.

According to an exemplary embodiment, the inorganic binder may exhibit an amorphous characteristic.

A second aspect of the present disclosure provides a method for preparing a catalyst, comprising the steps of:

a) subjecting an MFI-type first zeolite having a silica-alumina ratio (SAR) of 10 to 200 to ion exchange with a palladium (Pd) precursor to form an MFI-type first zeolite containing palladium (Pd) in the pores thereof;

b) forming a mixed support comprising: the palladium-containing MFI-type first zeolite; and a second zeolite having a silica-alumina ratio (SAR) of 10 to 200 and a pore size of 6 to 9 Å;

c) introducing to the mixed support at least one first metal selected from the group consisting of platinum (Pt), rhenium (Re) and molybdenum (Mo); and d) reducing the mixed support to afford a reduced form of palladium, followed by additionally reducing or sulfiding the first metal to form a reduced form of palladium and a reduced form of the first metal, or a reduced form of palladium and a sulfide form of the first metal in the mixed support;

wherein, the first metal is used in an amount of 0.01 to 5% by weight, based on the total weight of the catalyst.

A third aspect of the present disclosure provides a method for preparing a catalyst, the method comprising the steps of:

a1) subjecting an MFI-type first zeolite having a silica-alumina ratio (SAR) of 10 to 200 to ion exchange with a palladium (Pd) precursor to form an MFI-type first zeolite containing palladium in the pores thereof;

b1) introducing at least one first metal selected from the group consisting of platinum (Pt), rhenium (Re) and molybdenum (Mo) to a second zeolite having a silica-alumina ratio (SAR) of 10 to 200 and a pore size of 6 to 9 Å to form a first metal-containing second zeolite;

c1) combining the palladium-containing MFI-type first zeolite and the first metal-containing second zeolite to form a metal-containing mixed support; and d1) reducing the metal-containing mixed support to give a reduced form of palladium, followed by further reducing or sulfiding the first metal to form a reduced form of palladium and a reduced form of the first metal, or a reduced form of palladium and a sulfide form of the first metal in the mixed support;

wherein, the first metal is used in an amount of 0.01 to 5% by weight, based on the total weight of the catalyst.

A fourth aspect of the present disclosure provides a method for preparing a catalyst, the method comprising the steps of:

a2) subjecting an MFI-type first zeolite having a silica-alumina ratio (SAR) of 10 to 200 to ion exchange with a palladium (Pd) precursor to form an MFI-type first zeolite containing palladium (Pd) in the pores thereof;

b2) providing a second zeolite having a silica-alumina ratio (SAR) of 10 to 200 and a pore size of 6 to 9 Å;

c2) combining the palladium-containing MFI-type first zeolite, the second zeolite, and at least one first metal selected from the group consisting of platinum (Pt), rhenium (Re) and molybdenum (Mo) to form a metal-containing mixed support; and d2) reducing the metal-containing mixed support to form a reduced form of palladium, followed by further reducing or sulfiding the first metal to form a reduced form of palladium and a reduced form of the first metal, or a reduced form of palladium and a sulfide form of the first metal in the mixed support;

wherein, the first metal is used in an amount of 0.01 to 5% by weight, based on the total weight of the catalyst.

A fifth aspect of the present disclosure provides a method for preparing C8 aromatics, the method comprising the steps of:

providing a feedstock containing alkyl aromatics; and subjecting the feedstock to at least one reaction selected from disproportionation, transalkylation, and dealkylation in the presence of the catalyst as described above to give a product having an increased amount of C8 aromatic hydrocarbons, wherein the C8 aromatic hydrocarbons contain ethylbenzene at a content of less than 1.5% by weight.

According to an exemplary embodiment, the feedstock may comprises benzene, toluene, and/or C9+ aromatics.

BRIEF DESCRIPTION OF THE DRAWING

FIG. 1 is a conceptual view illustrating the distribution of palladium and a first metal, both acting as active metals, in a transalkylation catalyst according to an embodiment.

DESCRIPTION OF THE INVENTION

The present disclosure can be all accomplished by the following description. It is to be understood that the following description illustrates preferable embodiments of the present disclosure, but the present disclosure is not necessarily limited thereto. It is also to be understood that the accompanying drawings are included to provide a further understanding of the present disclosure and are not intended to limit the scope of the present disclosure.

The terms used herein are defined as follows.

The term "heterogeneous catalyst" refers to a catalyst that is present in a different phase from a reactant in a catalytic reaction. For example, a heterogeneous catalyst may remain undissolved in a reaction medium. When a heterogeneous catalyst is given, the reaction begins with the diffusion and adsorption of reactants onto the surface of the heterogeneous catalyst. After completion of the reaction, a product needs to be desorbed from the surface of the heterogeneous catalyst.

The term "support", as used herein, refers to a material (typically a solid-phase material) with a high specific surface area, to which a catalytically active component is attached, and the support may or may not be involved in a catalytic reaction.

As used herein, the term "active metal" refers to a metallic component directly responsible for progressing a desired reaction of the present disclosure, for example, hydrogenation of olefins, accounting, together with other components such as a support, for the catalyst.

As used herein, the term "disproportionation" refers to a desymmetrizing reaction of the same molecules in which an alkyl radical is transferred from one molecule to the other to form two different products. For example, disproportionation of toluene may result in producing benzene and xylene.

In a narrow sense, the term "transalkylation" refers to a reaction in which at least one alkyl radical (e.g., methyl, ethyl, propyl, butyl, and so on) is transferred from any organic compound to another.

The term "dealkylation" refers to a reaction in which at least one alkyl radical (e.g., methyl, ethyl, propyl, butyl, and so on.) is eliminated from a hydrocarbon compound (specifically, an aromatic compound).

The term "C9+ aromatic" refers to an aromatic hydrocarbon of C9 or more carbon atoms.

The term "C7− aromatic" refers to an aromatic hydrocarbon of C7 or less carbon atoms.

Disproportionation/Transalkylation/Dealkylation Catalyst

As described above, the catalyst provided according to an embodiment is a heterogeneous catalyst that can convert a feedstock containing alkyl aromatic compounds to C8 aromatic compounds. The catalyst has a metal incorporated into a mixed support including at least two kinds of zeolites. In this regard, the at least two kinds of zeolites may comprise (i) an MFI-type zeolite (a first zeolite) containing a reduced form of palladium (Pd) within the pores and/or crystalline (lattice or framework) structure thereof, and (ii) a second zeolite having a predetermined pore size (specifically, 6 to 9 Å).

In an embodiment, the MFI-type zeolite accounting for the mixed support is representatively exemplified by ZSM-5. ZSM-5 is a synthetic zeolite classified as MFI framework topology and characterized by a three-dimensional pore system with intersection double 10-membered ring straight and zigzag channels, and its chemical formula per unit cell is $(H, Na)_n[Al_nSi_{96-n}O_{192}]$. The size of the pores is less than about 6 Å and more specifically 0.51×0.55 nm (5.1×5.5 Å) for straight channels and 0.53×0.56 nm (5.3×5.6 Å) for zigzag channels.

The silica-alumina ratio (SAR) of MFI-type zeolite is a factor that affects the catalytic activity. Thus, it might be advantageous to employ an MFI-type zeolite that has a silica-alumina ratio range properly adjusted to improve the production yield of C8 aromatics (inter alia, mixed xylene). In this context, the first zeolite, particularly, ZSM-5 may have an SAR range of, for example, about 10 to 200, particularly about 20 to 100, and more particularly about 25 to 50.

According to an embodiment, the MFI-type zeolite (first zeolite) contains palladium within its pores and/or crystalline (lattice or framework) structure. With reference to FIG. 1, palladium (blue) is located inside the pores of the first zeolite in the mixed support while the first metal component (red) is distributed or located outside the unit cell of the first zeolite or at the voids between the zeolite crystalline particles and the binder.

In addition, the palladium may be in a reduced form (or an elemental form with the oxidation number 0). The reason why a reduced form of palladium is contained within the first zeolite is that when in a sulfide form, palladium decreases in hydrogenation function. Given the catalyst with a reduced hydrogenation function, the olefins which are present in the feedstock or which have been produced during the reaction cannot be effectively hydrogenated, and, thus combine again with aromatic compounds to form ethylbenzene, with the insufficient reduction of ethylbenzene in the product. In addition, the product may be converted back to C9+ aromatics. Furthermore, when being difficult to rapidly convert to paraffins, a large amount of the olefins thus formed reacts with aromatics to form polycyclic aromatics, e.g., aromatic compounds having two or more benzene rings, such as naphthalenes, which deactivate the catalyst. The polycyclic aromatics gradually turn to cokes, which are fatal to the function of the catalyst.

As described above, even when sulfidation is performed in a subsequent step, the palladium located inside the pores or crystalline structure of MFI-type zeolite is not converted to its sulfide form, but retains a reduced state whereas only the metal introduced or supported on the surface of the mixed support or at in a vicinity thereof, that is, the first metal (or the first and the second metal) is converted to a sulfide. This behavior makes the catalyst different from the conventional transalkylation catalysts in which hydrogenation meal is supported only outside the pores of zeolite or on the binder.

According to an exemplary embodiment, the content of palladium in the first zeolite may range from about 0.001 to 0.25% by weight, particularly from about 0.003 to 0.1% by weight, and more particularly from about 0.005 to 0.05% by weight, based on the total weight of the first zeolite. When the content of palladium in the pores or crystalline structure of the first zeolite is less than the desired level, the catalyst has difficulty in effectively eliminate the olefins generated in the conversion of aromatics (e.g., dealkylation) or brings about insufficient reduction of ethylbenzene in the product. In contrast, when present in too much an amount, palladium cannot guarantee an additional ethylbenzene reduction effect, but rather may cause excessive hydrogenation, which results in a loss of aromatics such as benzene, etc. Thus, it may be advantageous to set the content of palladium within the aforementioned range. However, the ranges should be understood to be illustrative.

According to an embodiment, a second zeolite with a pore size of about 6 to 9 Å accounts for a different zeolite component of the mixed support. In an exemplary embodiment, the second zeolite may have an SAR of about 10 to 200, particularly about 15 to 150, more particularly about 20 to 100. Representative of the second zeolite having the aforementioned pore properties are mordenite (MOR) and beta-zeolite, each having a 12-membered ring pore structure. These zeolites may be used alone or in combination. In addition, the second zeolite may be a hydrogen form of mordenite (H-MOR) and/or a hydrogen form of beta-zeolite (H-BETA). With respect to detailed information on mordenite and beta-zeolite, reference may be made to Atlas of Zeolite Framework Types, 5th Revised Edition, Elsevier (2001), the entire content of which is incorporated herein by reference.

As described above, a catalyst according to an embodiment employs a mixed support composed of a first zeolite (containing palladium) and a second zeolite, wherein the palladium-containing first zeolite and the second zeolite may be mixed at a ratio of, for example, 1:about 1 to 9, particularly 1:about 1.5 to 8, and more particularly 1:about 2 to 6 (based on weight of zeolite).

For ease of catalyst fabrication, moldability may be introduced. In addition, the mixed support may further comprise an inorganic binder to provide the catalyst with sufficient strength and to reciprocally intimately bind, disperse, or mix the zeolite components. In an exemplary embodiment, the inorganic binder may be at least one selected from the group consisting of, for example, gamma-alumina, silica, silica-alumina, bentonite, kaolin, clinoptilolite, and montmorillonite. According to a particular embodiment, the inorganic binder may be amorphous and particularly, may be at least one selected from the group consisting of gamma-alumina, silica, and silica-alumina, and more particularly gamma-alumina and/or silica.

As such, when an inorganic binder is additionally employed, the mixed support may comprise, based on the total weight thereof, (i) the first zeolite in an amount of about 5 to 70% by weight (particularly, about 10 to 60% by weight, more particularly about 15 to 50% by weight), (ii) the second zeolite in an amount of about 10 to 90% by weight (particularly, about 20 to 80% by weight, more particularly about 30 to 70% by weight), and (iii) the inorganic binder in an amount of about 1 to 70% by weight (particularly, about 5 to 60% by weight, more particularly about 10 to 50% by weight).

According to an illustrative embodiment, a first metal having a hydrogenation function is supported on the mixed support. Unlike palladium, which is present within the pores or crystalline structure of the MFI-type zeolite (particularly, ZSM-5), as described above, the first metal is distributed over the outside (surface) of the zeolite in the mixed support or in a vicinity of the surface. The first metal may be at least one selected from the group consisting of platinum (Pt), rhenium (Re), and molybdenum (Mo). In addition, the first metal may be contained in an amount of about 0.01 to 5% by weight, particularly in an amount of about 0.01 to 3.5% by weight, more particularly in an amount of about 0.015 to 2.5% by weight, based on the total weight of the catalyst.

Meanwhile, the first metal may be in a reduced form, a partially oxidized form (for example, when the first metal is molybdenum (Mo), $Mo^{6+}$ is partially oxidized to $Mo^{4+}$), or a sulfide form.

In a particular embodiment, the first metal may be platinum. A reduced form of platinum may hydrogenate even aromatics as well as olefins due to the strong hydrogenation activity thereof. Thus, the first metal is controlled to have a proper level of hydrogenation activity by conversion of the first metal to a sulfide form, with the consequent suppression of the side reactions such as the hydrogenation of aromatics.

In another particular embodiment, the first metal may be rhenium wherein the rhenium may be in a reduced form or a sulfide form. When a reduced form of rhenium causes side reactions due to the excessive hydrogenation function thereof like platinum, rhenium may be introduced as a sulfide form.

In another particular embodiment, the first metal may be molybdenum wherein the molybdenum may be in the form of $MoO_2$ resulting from a partial reduction of $MoO_3$ (that is, a partially oxidized form) or in the form of a sulfide (that is, $MoS_2$). The reason is that molybdenum having an oxidation value of 6+ has low hydrogenation activity whereas an oxide or sulfide form of molybdenum having an oxidation value of 4+ can provide a hydrogenation function.

According to an exemplary embodiment, when the first metal has excessively high hydrogenation activity (for example, excessive hydrogenation activity is accounted for by only the first metal supported), a second metal may be introduced, together the first metal, into the mixed support to adjust the hydrogenation activity. Particularly for platinum, which has high hydrogenation activity, a second metal may be advantageously introduced, as necessary, into the catalyst with the aim of controlling the hydrogenation activity of platinum to suppress the generation of naphthene caused by the hydrogenation of an aromatic ring. In this regard, the second metal may be at least one selected from the group consisting of tin (Sn) and lead (Pb).

According to an exemplary embodiment, the second metal may be introduced in an amount in the range of about 0.01 to 5% by weight, particularly about 0.1 to 3% by weight, more particularly about 0.2 to 1% by weight, based on the total weight of the catalyst. The atomic ratio of the first metal:the second metal may be controlled within the range of, for example, 1:about 0.5 to 50, particularly 1:about 5 to 40, more particularly 1:about 10 to 20.

In a particular embodiment, a second metal may be used in combination with platinum serving as the first metal. When the relative amount of the second metal supported is excessively low or high, the platinum (especially, a reduced form) has undue hydrogenation activity or cannot exhibit a proper hydrogenation function, which results in causing a side reaction or decreasing the yield of mixed xylene and forming cokes, respectively. Thus, the amount of the supported second metal is advantageously controlled to fall within the ranges as appropriate. However, these ranges can be understood as exemplary.

According to an exemplary embodiment, the first and the second metal may be introduced as an alloy form on the mixed support and alternatively may be dispersed or distributed over the mixed support, with spaces apart from each other. Even when spaced apart from each other, the first and the second metal may be advantageously dispersed as adjacent to each other as possible to affect each other electrically and/or chemically.

It is noted in this embodiment that the introduction of a reduced form of palladium into the pores of MFI-type zeolite can increase the yield of mixed xylene, while minimizing the generation of ethylbenzene in the process of producing C8 aromatics from a feedstock containing aromatic hydrocarbons. Without being bound by a specific theory, the present disclosure may be described as follows.

According to the embodiment, the pore size of the first zeolite (ZSM-5) in the mixed support makes it difficult for C9+ aromatics in the feedstock to approach the inside of the pores, which is a main active site, during the dealkylation accompanied in the reaction process. In contrast, the second zeolite has relatively large pore sizes (e.g., about 6 to 9 Å) enough to allow for dealkylation in the pores thereof. In addition to dealkylation, the second zeolite allows disproportionation between toluene molecules, transalkylation between toluene and C9 aromatic compounds, dealkylation of alkyl aromatic compounds, and transalkylation between benzene and C9+ aromatic compounds, simultaneously, in the pores.

Meanwhile, monoalkyl benzenes, which are relative small in molecular size, can approach the inside of the first zeolite pores less than 6 Å in size as well as the second zeolite pores, so that the dealkylation of monoalkyl benzenes can occur even in the first zeolite. Monoalkyl benzenes can be converted to ethylene and benzene, or to propylene and benzene by dealkylation. The olefins thus formed (ethylene, propylene, etc.) tends to react with the aromatics, again. Thus, the olefins, if not immediately hydrogenated, may not only re-alkylate aromatic compounds, lowering conversion of C9+ aromatic compounds as well as monoalkyl benzenes, but also themselves undergo a polymerization reaction to promote the formation of cokes, which cause the catalyst to be deactivated. Furthermore, the olefins cause the increase of formation of ethylbenzene among C8 aromatics. Therefore, there is a need for introducing a hydrogenation metal or metals in addition to the zeolite components to the catalyst.

Taking into account this circumstance, a hydrogenation metal or metals are introduced in two ways to the catalyst in the present embodiment. In brief, a reduced form of palladium is introduced inside the pores of the first zeolite. A sulfide form of palladium (palladium sulfide) has a weak hydrogenation function to slowly carry out hydrogenation of olefins and as such, can poorly lower ethylbenzene in the product C8 aromatics. Hence, palladium is introduced inside the pores of the first zeolite and then remains in a reduced state during conversion of the first metal having a hydrogenating function to a sulfide, thereby effectively hydrogenating the olefins. In addition, the first metal may be supported in a reduced state, a partially oxidized state, or a sulfide state on the mixed support. Optionally, a second metal may be employed in order to control hydrogenation activity of the first metal, whereby the catalyst can increase the yield of C8 aromatics and remarkably lower ethylbenzene contents in the reaction products, with the simultaneous suppression of coke formation.

According to the present embodiment, a metal that does not exhibit excessive hydrogenation activity, but can easily conduct ion exchange may be advantageously chosen to be supported inside the pores (or crystalline structure) of the first zeolite. In this regard, after being introduced (e.g., through an ion exchange) inside the first zeolite and then reduced, platinum or rhenium as hydrogenation metal may convert aromatic compounds to naphthene, light gas, etc. due to the excessive hydrogenating activity thereof. As for molybdenum, it has difficulty in conducting an ion exchange when being in a dissolved state in a solvent. In light of the above, a reduced form of palladium is introduced inside the pores of the first zeolite (e.g., MFI-type zeolite) while other hydrogenation metal (or metals) is supported on the mixed support.

In an exemplary embodiment, the catalyst may be in a powder form. More generally, however, the catalyst may be prepared in a form of shaped (or molded) body with the aid of a binder, and then the shaped body is loaded into a fixed bed reactor. The shaped body may take versatile morphologies known in the art, for example, granules, pellets, tablets, cylinders, spheres, etc.

Preparation Method for Catalyst

According to an embodiment, a disproportionation/transalkylation/dealkylation catalyst is prepared as follows.

Preparation of Palladium-Containing MFI-Type Zeolite

First, palladium is introduced into the pores or crystalline structure of MFI-type zeolite, particularly ZSM-5 as a first zeolite.

ZSM-5 is generally synthesized in a sodium form. As illustrated in the following reaction scheme 1, the sodium form can undergo ion exchange with an ammonium ion-containing compound such as ammonium nitrate, ammonium chloride, etc.

[Reaction Scheme 1]

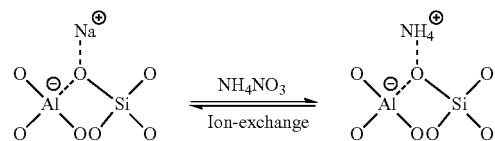

In an exemplary embodiment, an ammonium form of ZSM-5 ($NH_4$-ZSM-5) may be employed. Alternatively, an ammonium form of ZSM-5 may be converted to a hydrogen form (H-ZSM-5) by thermal treatment such as sintering. In this regard, the reason why ZSM-5 is converted to an ammonium form or a hydrogen form is because a sodium form cannot guarantee acid (solid acid) catalyst activity. Furthermore, it may be advantageous to convert ZSM-5 to a hydrogen form in the catalyst preparation process or the catalyst pre-treatment process before the reaction. In addition, as stated above, ZSM-5 may have an SAR of about 10 to 200, particularly about 20 to 100, more particularly about 25 to 50.

In order to introduce palladium inside the pores or crystalline structure thereof, ZSM-5 (ammonium form or hydrogen form) provided as described above is subjected to ion exchange reaction with a palladium precursor.

The term "ion exchange reaction" of zeolite refers to an exchange reaction between a non-framework element and/or molecule on zeolite and other element (or elements) and/or molecule (molecules), such as a metal, and detailed technical information is known in the art. For example, reference may be made to various documents including U.S. Pat. Nos. 3,140,249 and 3,140,251, the entire contents of which are incorporated herein by reference.

According to an exemplary embodiment, the palladium precursor may be in a form of organic salt or inorganic salt, a palladium complex, or a combination thereof. Examples of the palladium precursor include palladium acetate, palladium chloride, palladium bromide, palladium nitrate, palladium sulfate, palladium carbonate, palladium hydroxide, palladium halide, tetramine palladium nitrate, tetramine palladium chloride, and ammonium tetrachloropalladate. These precursors may be used alone or in combination. It should be understood that the enumerated palladium precursors are illustrative. More particularly, tetramine palladium nitrate may be employed.

According to an exemplary embodiment, an ion exchange reaction may be conducted by adding an MFI-type zeolite (e.g., ZSM-5) to a solution of the palladium precursor in an aqueous medium (i.e., water) or an organic solvent. Examples of the organic solvent include, but are not limited to, acetic acid, acetone, acetonitrile, benzene, 1-butanol, 2-butanol, 2-butanone, t-butanol, chlorobenzene, chloroform, cyclohexane, 1,2-dichloroethane, diethylether, diethylene glycol, diglyme, 1,2-dimethyoxy-ethane, dimethylether, dimethyl-formamide, dimethyl sulfoxide, dioxane, ethanol, ethylacetate, ethylene glycol, glycerin, heptane, hexamethyl phosphoamide, hexamethyl phosphorous triamide, hexane, methanol, methyl t-butyl ether, methylene chloride, N-methyl-2-pyrrolidinone, nitromethane, pentane, 1-propanol, 2-propanol, pyridine, tetrahydrofuran, toluene, and triethyl amine.

According to an exemplary embodiment, the ion exchange reaction may be conducted by adding ZSM-5 to the palladium precursor solution and contacting them at a temperature of, for example, about 25 to 100° C., particularly about 40 to 100° C., and more particularly about 60 to 95° C. for about 0.5 to 48 hours, particularly about 1 to 24 hours, and more particularly about 3 to 12 hours. The solvent in the palladium precursor solution (specifically, the aqueous palladium precursor solution) may be used in an amount about 0.5 to 20 times, particularly about 1 to 10 times, and more particularly about 2 to 5 times as large as the weight of ZSM-5. In addition, the palladium precursor solution for ion exchange may range in concentration from about 0.0001 to 1 M (particularly from about 0.001 to 0.5 M, more particularly from about 0.002 to 0.3 M), without limitations thereto. The concentration may be determined depending upon the ion exchange amount of palladium. In addition, multiple rounds of the ion exchange may be conducted in order to introduce a desired amount of palladium.

The ZSM-5 that has been subjected to ion exchange with palladium as described above (e.g., Pd-ZSM-5) may undergo a typical post-treatment process. For example, the liquid is removed by filtration. Then, the ion-exchanged ZSM-5 is dried and/or sintered. By way of example, the drying temperature may range from about 60 to 200° C. (particularly about 80 to 150° C.) and the drying time may be adjusted within about 0.5 to 15 hours (particularly about 1 to 12 hours). In addition, the sintering process may be conducted in, for example, an oxygen-containing atmosphere (e.g., pure oxygen or air) and/or in an inert gas (e.g., helium, nitrogen, argon, or a combination thereof)-containing atmosphere at a temperature of about 300 to 800° C. (particularly about 400 to 650° C.). In addition, the sintering may be continued for about 0.5 to 24 hours (particularly about 1 to 2 hours). It should be understood that the above-mentioned drying and/or sintering conditions are illustrative.

Preparation of Catalysis Body

Subsequent to preparation of the palladium-containing first zeolite (Pd-ZSM-5), a step of preparing a catalyst body may be performed by loading or supporting a first metal (or a first metal and a second metal) during or after the combination of the first zeolite and the second zeolite (or second zeolite and binder) in various manner as follows:

(i) After the palladium-containing first zeolite and the second zeolite are combined to form a mixed support, a first metal (or a first metal and a second metal) may be supported onto the mixed support.

As described above, the second zeolite may have a pore size of 6 to 9 Å. In addition, the second zeolite may have an SAR of, for example, about 10 to 200, particularly about 15 to 150, and more particularly about 20 to 100.

In an exemplary embodiment, a mixing ratio of palladium-containing first zeolite:second zeolite (based on weight of zeolite) may be adjusted within a range of, for example, 1:about 0.3 to 10, particularly 1:about 1 to 8, and more particularly 1:about 2 to 6. The mixed support may be in a powder form.

According to an exemplary embodiment, an inorganic binder may be combined (mixed) at a predetermined ratio with the first zeolite and the second zeolite to form a mixed support in a shaped (or molded) form. To this end, the combination or mixture may be molded using conventional techniques such as extrusion, spray drying, pelletizing, oil dropping, etc.

According to an exemplary embodiment, the mixed support may have an apparent packing density of about 0.4 to 0.9 cc/g, particularly about 0.45 to 0.85 cc/, and more particularly about 0.5 to 0.8 cc/g. In addition, the mixed support may range in average pore size, for example, from about 20 to 200 Å, particularly from about 25 to 150 Å, and more particularly from about 30 to 100 Å. Meanwhile, the mixed support may have a pore volume of, for example, about 0.1 to 1 cc/g, particularly about 0.15 to 0.7 cc/g, and more particularly about 0.2 to 0.5 cc/g. In addition, the mixed support may have a specific surface area (BET) of, for example, about 200 to 700 $m^2/g$, particularly about 250 to 600 $m^2/g$, and more particularly about 300 to 550 $m^2/g$. It should be understood to a person skilled in the art that the numerical ranges for the physical properties are illustrative.

According to an exemplary embodiment, the mixed support, especially the shaped mixed support may be cylindrical in morphology, having the dimensions of, for example, about 0.5 to 5 mm (particularly about 1 to 3 mm) in diameter and about 3 to 20 mm (particularly about 5 to 15 mm) in length. In addition to a cylindrical form, the shaped mixed support may be in a granular, pellet, tablet, or spherical form.

Subsequent to the preparation of the mixed support, a step of supporting a first metal having a hydrogenating function (or a first metal and a second metal) outside the pores or crystalline structure of the zeolite may be conducted.

The first metal may be at least one selected from the group consisting of platinum (Pt), rhenium (Re), and molybdenum (Mo). In order to introduce the first metal, any techniques known in the art may be applied, as exemplified by co-precipitation, impregnation (e.g., initial wet impregnation, excess water impregnation, and immersion), and so on.

According to a particular embodiment, the first metal (or the first and the second metal) may be introduced to the mixed support through the impregnation technique using a metal precursor (typically a water-soluble or solvent-soluble metal compound).

In this regard, at least one selected from hydrides, fluorides (e.g., $PtF_6$, $PtF_4$, $[PtF_5]_4$, etc.), chlorides (e.g., $H_2PtCl_6$, $PtCl_3$, $PtCl_4$, $Pt_6Cl_{12}$, etc.), bromides (e.g., $PtBr_3$, $PtBr_4$, etc.), iodides (e.g., $PtI_2$, $PtI_3$, $PtI_4$, etc.), oxides (e.g., PtO, $PtO_2$, PtO, etc.), sulfides (e.g., PtS, $PtS_2$, etc.), carbonyls (e.g., $Pt(CO)_4$) and/or complexes (e.g., $[PtCl_2(NH_3)_2]$. $[PtCl_2(NH_3)_2]$, $K_2[PtCl_6]$. $K_2[Pt(CN)_4]$, $PtCl_4 \cdot 5H_2O$, $K[PtCl_3(NH_3)]$, $Na_2[PtBr_6] \cdot 6H_2O$, $(NH_4)_2[PtBr_6]$, $K_2[PtI_6]$, $(NH_4)_2[PtCl_6]$, $K_2[Pt(CN)_6]$, $(NH_4)_2[PtCl_4]$, $K_2[Pt(NO_2)_4]$, $K[PtCl_3 (C_2H_4)] \cdot H_2O$ $[Pt(NH_3)_4](NO_3)_2 \cdot H_2PtCl_6$, etc.) may be available as the platinum precursor, but without limitations thereto. For a molybdenum precursor, for example, at least one selected from molybdenum (II) acetate, ammonium (VI) molybdate, diammonium (III) dimolybdate, ammonium (VI) heptamolybdate, ammonium (VI) phosphomolybdate and similar sodium and potassium salts, molybdenum (III) bromide, molybdenum (III)-(V) chloride, molybdenum (VI) fluoride, molybdenum (VI) oxychloride, molybdenum (IV)-(VI) sulfide, molybdic acid and corresponding acid ammoniums, sodium and potassium salts, molybdenum (II-VI) oxide, and the like may be used, but is not limited thereto. At least one selected from perrhenic acid, ammonium perrhenate, rhenium oxide complexes, $ReO_2$, $ReO_3$, and $Re_2O_7$ is available as a rhenium precursor, but without limitations thereto.

In addition, the second metal employed to control the hydrogenation activity of the first metal may be introduced simultaneously with the first metal or sequentially (before or after the first metal).

For use in the second metal, a tin precursor may be at least one selected from tin chloride, tin bromide, tin iodide, tetramethoxy tin, tetraethoxy tin, tetrabutoxy tin, tetraphenoxy tin, tin sulfide, tin oxide, tin sulfate, tin nitrate, tin selenide, tin peroxide, $Na_2SnO_3$, $Na_2SnO_3 \cdot 3H_2O$, $Sn(OH)_2$, tin nitride, tin acetate, tin oxalate, and the like. In addition, a lead precursor may be at least one selected from lead nitrate, lead chloride, lead carbonate, $Pb(acac)_2$, lead acetate, and the like.

According to an exemplary embodiment, the first metal and/or the second metal in the impregnation solution may range in concentration, for example, from about 0.005 to 1 M, particularly from about 0.01 to 0.5 M, and more particularly from about 0.015 to 0.3 M. The conditions for impregnation are not particularly limited, however, for example, impregnation may be performed at about 1 to 100° C. (particularly about 25 to 60° C.) for about 0.1 to 48 hours (about 0.5 to 12 hours). These conditions should be understood as illustrative.

(ii) The first metal (or the first metal and the second metal) may be first supported onto the second zeolite, and then the metal-supported second zeolite may be combined with the palladium-containing first zeolite. This approach is substantially identical to the foregoing manner (i) in terms of all conditions, with the exception that the first metal is impregnated onto the second zeolite prior to combining the palladium-containing first zeolite with the second zeolite. In addition, when the palladium-containing first zeolite and the first metal-containing second zeolite are combined with each other, an inorganic binder may be combined together, as described above. Moreover, the first metal and the second metal may be introduced, together (simultaneously), to the second zeolite. Alternatively, the second metal can be introduced after combining the palladium-containing first zeolite with the first metal-containing second zeolite.

(iii) During the process of combining (mixing or kneading) the palladium-containing first zeolite with the second zeolite, the first metal (or first metal and second metal) may be introduced. The other conditions are as described above. In this case, the first metal is introduced during the combination process of the first zeolite and the second zeolite to form a metal-containing mixed support, followed by introducing the second metal thereto.

After being formed by introducing the first metal (or the first and the second metal) to the mixed support as described above, the catalyst body may undergo any typical post-treatment processes such as water washing.

Further, a drying step may be conducted as post-treatment. For example, the catalyst body may be dried in an oxygen-containing atmosphere (particularly air), with the drying temperature set to be, for example, about 60 to 200° C. and particularly about 80 to 150° C. In addition, the drying time may be determined in the range of, for example, about 0.5 to 15 hours and particularly about 1 to 12 hours.

Then, a step of sintering (or heat-treating) the dried catalyst body may be performed. The sintering step may be performed in an oxygen-containing atmosphere (e.g., air) or an inert gas (e.g., nitrogen or the like) atmosphere under a temperature condition of about 300 to 800° C. and particularly about 400 to 650° C. In addition, the sintering time may be controlled in the range of, for example, about 0.5 to 24 hours and particularly about 1 to 12 hours.

Reduction Step

According to an embodiment, a step of reducing the sintered catalyst body may be performed. For the reduction step, hydrogen may be used alone or diluted with an inert gas (e.g., $N_2$, He, Ar, or the like) before use. The reduction step may be performed at a temperature of, for example, about 25 to 800° C., particularly about 200 to 700° C., and more particularly about 300 to 550° C. The reduction treatment time may be controlled in the range of, for example, about 0.5 to 24 hours, and particularly about 1 to 12 hours, but is not particularly limited thereto.

Through the reduction step, the metals (mainly palladium) distributed inside the pores of zeolite in the mixed support or the metals (mainly the first metal, or the first and the second metal) distributed outside the pores can be converted to reduced forms. As such, the reduction step may be conducted in at least one stage, and particularly in multiple stage. In this case, the palladium may be reduced in a primary reduction stage, followed by additional reduction of the first metal through a secondary reduction stage. The primary and the secondary reduction stage may be different from each other in terms of reduction conditions (e.g., temperature).

Through the processed described above, the palladium and the first metal may exist as respective reduced forms. For example, the metals contained in the catalyst may be in elemental forms through the reduction treatment and may act as catalytic components responsible for the following disproportionation/transalkylation/dealkylation.

Sulfidation (or Sulfurization) Step

In order to control the hydrogenation activity of the first metal depending on the reduction state thereof, for example, to regulate excessive hydrogenation activity resulting in inducing side reactions such as loss of aromatics, etc. (particularly, for platinum and rhenium) or to impart a hydrogenation activity to the first metal (particularly for molybdenum), a step of converting the metal to a sulfide form rather than a reduced form may be additionally conducted as necessary. According to an exemplary embodiment, sulfidation may be conducted after palladium is reduced (for example, after the primary reduction stage or after the primary and the secondary reduction stages). As a result, the palladium becomes reduced while the first metal (or the first metal and the second metal) may exist as a sulfide.

In this regard, a metal component in a catalyst body can be converted into a sulfide by any methods known in the art. Such sulfidation can be performed in a gas-phase manner (contacting with hydrogen sulfide or a mixture of hydrogen sulfide and an inert gas) or in a liquid-phase manner (contacting with a sulfur compound-containing solution). According to a particular embodiment, the reduced catalyst body may be treated with a solution containing a sulfur compound.

According to an exemplary embodiment, a sulfur compound available for the sulfidation may be at least one selected from hydrogen sulfide, hydrogen disulfide, carbon disulfide, and alkyl sulfide. In particular, the alkyl sulfide may be exemplified by methyl sulfide, dimethyl sulfide, dimethyl disulfide, diethyl sulfide, and/or dibutyl sulfide. In addition, a hydrocarbon-based solvent, such as benzene, toluene, xylene, a C9+ aromatic, hexane, and heptane, may be used as a solvent for the sulfidation. In an exemplary embodiment, the amount of a sulfur compound in the solution for sulfidation may be properly determined to be an equivalent weight necessary for sulfiding the metal in the catalyst body or higher. For example, when molybdenum is used as the first metal, a sulfur compound having an equivalent weight necessary for sulfiding molybdenum to $MoS_3$ (may be finally converted into $MoS_2$) or higher may be mixed in a solution before use.

In an exemplary embodiment, the sulfidation may be performed at a temperature of about room temperature to 500° C. (particularly about 100 to 450° C.) for about 0.5 to 100 hours (particularly about 1 to 48 hours).

It should be noted that the first metal (or the first metal and the second metal) is converted to its sulfide form whereas the palladium contained inside the pores of the first zeolite is not. Without being bound to a specific theory, the palladium introduced inside the pores of the first zeolite exists as its reduced form (elemental palladium) as a result of the reduction step and is not thereafter converted into a sulfide even when being in contact with a sulfur component, but sulfur exists while adsorbing onto the surface of the palladium. In this context, when the feeding of the sulfur component is blocked, the sulfur component is detached under the reaction condition so that the palladium remains in a reduced state.

Reactions for Producing C8 Aromatics

Provided according to an embodiment is a process in which a feedstock containing aromatics, especially, alkyl aromatics is converted to C8 aromatic hydrocarbons by a reaction using the above-described catalyst.

In this regard, the alkyl aromatics bear an aromatic ring having at least one alkyl radical attached thereto. Examples of the alkyl radical include methyl, ethyl, propyl, and butyl. The alkyl aromatics may be exemplified by toluene, ethyl toluene, propyl benzene, tetramethyl benzene, ethyldimethyl benzene, diethyl benzene, methylpropyl benzene, ethylpropyl benzene, triethyl benzene, diisopropylbenzene, and a mixture thereof.

In addition, the feedstock may further contain aromatics having no alkyl substituents thereon, such as benzene as well as the above-described alkyl aromatics. In an exemplary embodiment, the feedstock may contain benzene, toluene, and/or C9+ aromatics. However, it is not excluded that C8+ aromatics (e.g., ortho-xylene, meta-xylene, para-xylene, ethyl benzene, and the like) are contained in the feedstock. Therefore, the feedstock may contain toluene or C9+ aromatic compounds (particularly, C9 and/or C10 aromatic compounds) alone or in a mixture thereof at any ratio or may contain benzene, toluene, and C9+ aromatics in combination.

According to an exemplary embodiment, the feedstock containing alkyl aromatics may be derived from: catalytic reformation of naphtha; thermal cracking of naphtha, distillates, or other hydrocarbons for production of light olefins and aromatic-rich fractions; and catalytic or thermal cracking of heavy oil fractions for production of hydrocarbons having a gasoline boiling point range. Such sources may be used alone or in combination as a feedstock. Optionally, such reactant sources may be subjected to any pre-treatment process known in the art, such as hydrotreating, prior to the reaction, for the purpose of eliminating impurities (e.g., any ingredients that can affect catalytic activity and product distribution, such as sulfur and olefins).

According to an embodiment, a feedstock containing alkyl aromatics may undergo at least one reaction of disproportionation, transalkylation, and dealkylation in a predetermined reaction condition. For instance, there are disproportionation of toluene, transalkylation of toluene/C9 aromatic compounds, and dealkylation of alkylaromatics, and a C8 aromatic compound may be produced through the above-described reactions.

According to an exemplary embodiment, the above-described reactions may be performed in a gas phase or a liquid phase under hydrogen supply, wherein the molar ratio of hydrogen/hydrocarbon may be controlled in the range of, for example, about 0.1 to 20 particularly about 0.5 to 7, and more particularly about 1 to 5. So long as it is known in the art, any reactor, for example, a fixed bed reactor, a batch reactor, a semi-batch reactor, a fluidized bed reactor, a slurry reactor, and the like, may be used.

Meanwhile, the above-described reaction may be performed in conditions of, for example, a temperature of about 200 to 600° C. (particularly about 250 to 550° C. and more particularly about 300 to 500° C.) and a pressure of about 5 to 100 kgf/cm$^2$ (particularly about 10 to 80 kgf/cm$^2$ and more particularly about 20 to 60 kgf/cm$^2$). These reaction conditions should be understood as illustrative and thus can be changed depending on the composition of the feedstock, and the like.

According to another embodiment, the reaction may be performed in a continuous mode where the weight hourly space velocity (WHSV) may be controlled within the range of, for example, about 0.1 to 20 hr$^{-1}$, specifically about 1 to 10 hr$^{-1}$, and more specifically about 2 to 5 hr$^{-1}$, but these should be understood as exemplary.

According to the present embodiment, the alkyl aromatic-containing feedstock is converted into C8 aromatics via disproportionation/transalkylation/dealkylation in the presence of the catalyst as described above. Specifically, it is notable that the catalyst of the present disclosure can maintain an advantageous production yield of C8 aromatics and a remarkably low content of ethylbenzene in the C8 aromatic hydrocarbons, compared to the conventional zeolite-based transalkylation catalysts. The content of ethylbenzene in the C8 aromatics may be less than, for example, about 1.5% by weight, particularly about 1.3% by weight, and more particularly about 1% by weight.

A better understanding of the present disclosure may be obtained through the following examples which are set forth to illustrate, but are not to be construed as limiting the present disclosure.

EXAMPLES

Materials used in the Examples are as follows.

ACS reagent grade metal compounds were purchased from Sigma-Aldrich. Zeolites were purchased from Zeolyst. In addition, raw materials used in commercial processes were used for disproportionation/transalkylation/dealkylation.

Comparative Example 1

HZSM5/H-MOR/Pt—Sn Catalyst and Disproportionation/Transalkylation Using Same

Hydrogen type mordenite with a silica-alumina ratio (SAR) of 20 and hydrogen type ZSM-5 with a silica-alumina ratio (SAR) of 30 were molded using gamma-alumina as an inorganic binder to give a shaped body. In the course of shaping, an aqueous $H_2PtCl_6$ solution (0.0154 M) and aqueous $SnCl_2$ solution (0.084 M) were mixed therewith, wherein the mixed support except for platinum and tin was controlled to comprise 55% by weight of the mordenite and 25% by weight of ZSM-5 while platinum and tin were supported in an amount of 0.03 parts by weight and 0.4 parts by weight, respectively, based on total 100 parts by weight of the mordenite/ZSM-5/inorganic binder. The shaped body was in a cylindrical form with a diameter of 1.6 mm and a length of 3 mm. Then, the shaped body was dried at 150° C. for 10 hours, followed by sintering at 500° C. for 3 hours to prepare a catalyst body.

2.0 g of the catalyst body thus obtained was loaded in a continuous fixed bed reactor which was then purged with nitrogen and pressurized to 30 kg/cm$^2$. Subsequently, nitrogen was exchanged with hydrogen. While hydrogen was fed at a rate of 82 cc/min, the atmosphere in the reactor was maintained at 150° C. for 10 hours and then at 400° C. for 2 hours to reduce the catalyst body.

After the reduction treatment, the reactor was cooled to 350° C., and disproportionation/transalkylation was conducted with a feedstock containing 50% by weight of a C7– aromatic fraction composed mainly of toluene and 50% by weight of C9+ aromatic fraction composed mainly of C9 aromatics introduced thereto at a rate of 0.135 cc/min. The reaction results are summarized in Table 1, below.

Comparative Example 2

H-ZSM-5/H-MOR/Mo Catalyst and Disproportionation/Transalkylation Using Same

Hydrogen type mordenite with a silica-alumina ratio (SAR) of 20 and hydrogen type ZSM-5 with a silica-alumina ratio (SAR) of 30 were molded into a cylindrical form using gamma-alumina as an inorganic binder to give a shaped body. The shaped body contained 55% by weight of mordenite and 25% by weight of ZSM-5 and was dried as a mixed support at 150° C. for 10 hours before being sintered at 500° C. for 3 hours.

Next, an aqueous ammonium heptamolybdate solution (0.06 M) was used to impregnate 2.0 parts by weight of molybdenum per 100 parts by weight of the mixed support, followed by drying at 150° C. for 10 hours and then sintering at 500° C. for 3 hours.

2.0 g of the catalyst body thus obtained was loaded in a continuous fixed bed reactor which was then purged with nitrogen and pressurized to 30 kg/cm². Subsequently, the nitrogen was exchanged with hydrogen. While hydrogen was fed at a rate of 82 cc/min, the atmosphere in the reactor was maintained at 150° C. for hours to reduce the catalyst body. Subsequently, the temperature was elevated to 350° C. while toluene mixed with 0.01% by weight of DMDS (Dimethyl Disulfide) was fed at a rate of 0.15 cc/min for 6 hours to conduct sulfidation.

Thereafter, the catalyst body was subjected to disproportionation/transalkylation with a feedstock containing % by weight of a C7- aromatic fraction composed mainly of toluene and 50% by weight of C9+ aromatic fraction composed mainly of C9 aromatics introduced thereto at a rate of 0.135 cc/min. The reaction results are summarized in Table 1, below.

Comparative Example 3

H-ZSM-5/H-BEA/Re Catalyst and Disproportionation/Transalkylation Using Same

Hydrogen type beta-zeolite with a silica-alumina ratio (SAR) of 25 and hydrogen type ZSM-5 with a silica-alumina ratio (SAR) of 30 were molded into a cylindrical form using gamma-alumina as an inorganic binder to give a shaped body with 1.6 mm in diameter and 3 mm in length. The shaped body contained 55% by weight of beta-zeolite and 25% by weight of ZSM-5 and was dried as a mixed support at 150° C. for 10 hours before being sintered at 500° C. for 3.

Next, an aqueous ammonium perrhenate solution (0.06 M) was used to impregnate 0.5 parts by weight of rhenium per 100 parts by weight of the mixed support, followed by drying at 150° C. for 10 hours and then sintering at 500° C. for 3 hours to prepare a catalyst body.

The catalyst body thus obtained was pre-treated and used for disproportionation/transalkylation in the same manner as in Comparative Example 2 The reaction results are summarized in Table 1, below.

Comparative Example 4

Pd-MOR/H-ZSM-5/Mo Catalyst and Disproportionation/Transalkylation Using Same

An ammonium form of mordenite with a silica-alumina ratio (SAR) of 20 was subjected to ion exchange in an aqueous tetramine palladium nitrate solution (0.002 M) at 80° C. for 6 hours, followed by filtration and washing with water (deionized water). Thereafter, the ion-exchanged mordenite was dried at 150° C. for 10 hours and then sintered at 500° C. for 3 hours to give Pd-containing mordenite. The resulting Pd-containing mordenite was analyzed to contain Pd at a content of 0.018% by weight based on the weight of mordenite, as measured by ICP (PerkinElmer, Agilent 720).

A catalyst body was prepared in the same manner as in Comparative Example 2, with the exception of using Pd-containing mordenite instead of hydrogen type mordenite. The catalyst body thus obtained was pre-treated and used for disproportionation/transalkylation. The reaction results are summarized in Table 1, below.

TABLE 1

|  | C. Ex. 1 | C. Ex. 2 | C. Ex. 3 | C. Ex. 4 |
| --- | --- | --- | --- | --- |
| Rxn. Condition | Temp.: 350° C., Press.: 30 kg/cm², WHSV = 3.5 hr⁻¹, H₂/HC (Molar ratio):3 | | | |
| EB in XYL (%) | 1.71 | 2.53 | 3.01 | 2.42 |
| XYL Yield (%) | 36.10 | 34.65 | 34.43 | 34.71 |
| Bz Purity (%) | 99.89 | 99.82 | 99.77 | 99.80 |
| Conversion Rate (%) | 45.57 | 44.89 | 43.79 | 44.91 |

Example 1

Pd-ZSM-5/H-MOR/Pt—Sn (Pd Reduced, Pt Reduced) Catalyst and Disproportionation/Transalkylation Using Same An ammonium form of ZSM-5 with a silica-alumina ratio (SAR) of 30 was subjected to ion exchange in an aqueous tetramine palladium nitrate solution (0.002 M) at 80° C. for 6 hours, followed by filtration and washing with water (deionized water). Thereafter, the ion-exchanged ZSM-5 was dried at 150° C. for 10 hours and then sintered at 500° C. for 3 hours to give Pd-containing ZSM-5. The resulting Pd-containing ZSM-5 was analyzed to contain Pd at a content of 0.015% by weight based on the weight of ZSM-5, as measured by ICP.

A catalyst body was prepared in the same manner as in Comparative Example 1, with the exception of using Pd-containing ZSM-5 instead of hydrogen type ZSM-5.

2.0 g of the prepared catalyst body was loaded in a continuous fixed bed reactor which was then purged with nitrogen and pressurized to 30 kg/cm². Subsequently, the nitrogen was exchanged with hydrogen. While hydrogen was fed at a rate of 82 cc/min, the atmosphere in the reactor was maintained at 150° C. for 10 hours to reduce the catalyst body.

Thereafter, the temperature was elevated to 400° C. and maintained thereat for 2 hours to further reduce Pt in the catalyst body. After the reduction treatment, the reactor was cooled to 350° C. wherein disproportionation/transalkylation was conducted with a feedstock containing 50% by weight of a C7- aromatic fraction composed mainly of toluene and 50% by weight of C9+ aromatic fraction composed mainly of C9 aromatics introduced thereto at a rate of 0.135 cc/min. The reaction results are summarized in Table 2, below.

Example 2

Pd-ZSM-5/H-MOR/Mo (Pd: Reduced, Mo: Sulfided) Catalyst and Disproportionation/Transalkylation Using Same A catalyst body was prepared in the same manner as in Comparative Example 2, with the exception of using Pd-exchanged ZSM-5 prepared in Example 1 instead of hydrogen type ZSM-5.

2.0 g of the catalyst body thus prepared was loaded in a continuous fixed bed reactor which was then purged with nitrogen and pressurized to 30 kg/cm². Subsequently, the nitrogen was exchanged with hydrogen. While hydrogen was fed at a rate of 82 cc/min, the atmosphere in the reactor was maintained at 150° C. for hours to reduce the catalyst body. Subsequently, the temperature was elevated to 350° C.

while toluene mixed with 0.01% by weight of DMDS was fed at a rate of 0.15 cc/min for 6 hours to conduct sulfidation.

Thereafter, disproportionation/transalkylation was conducted with a feedstock containing 50% by weight of a C7-aromatic fraction composed mainly of toluene and 50% by weight of C9+ aromatic fraction composed mainly of C9 aromatics introduced thereto at a rate of 0.135 cc/min. The reaction results are summarized in Table 2, below.

Example 3

Pd-ZSM-5/H-BEA/Re (Pd: Reduced, Re: Sulfided) Catalyst and Disproportionation/Transalkylation Using Same A catalyst body was prepared in the same manner as in Comparative Example 3, with the exception of using the Pd-exchanged ZSM-5 prepared in Example 1 instead of hydrogen type ZSM-5.

The catalyst body thus obtained was pre-treated and used for disproportionation/transalkylation in the same manner as in Comparative Example 2. The reaction results are summarized in Table 2, below.

Example 4

Pd-ZSM-5/Pd-MOR/Mo(Pd: Reduced, Mo: Sulfided) Catalyst and Disproportionation/Transalkylation (Evaluation of Performance Depending on Pd-Containing Zeolites)

A catalyst body was prepared in the same manner as in Comparative Example 2, with the exception of using the Pd-exchanged mordenite prepared in Comparative Example 4 and the Pd-exchanged ZSM-5 prepared in Example 1 instead of hydrogen type mordenite and hydrogen type ZSM-5, respectively.

The catalyst body thus obtained was pre-treated and used for disproportionation/transalkylation in the same manner as in Comparative Example 2. The reaction results are summarized in Table 2, below.

Example 5

Pd-ZSM-5/H-MOR/Pt—Sn (Pd: Reduced, Pt: Sulfided) Catalyst and Disproportionation/Transalkylation Using Same The catalyst prepared in Example 1 was pre-treated and used for disproportionation/transalkylation in the same manner as in Example 2. The reaction results are summarized in Table 2, below.

Example 6

Pd(0.25)-ZSM-5/H-MOR/Mo (Pd: Reduced, Mo: Sulfided) Catalyst and Disproportionation/Transalkylation Using Same (Evaluation of Performance of Catalyst Having Excessive Pd-loading)

An ammonium form of ZSM-5 having a silica-alumina ratio (SAR) of 30 was subjected to ion exchange with an aqueous tetramine palladium nitrate solution (0.002 M) at 80° C. for 6 hours, followed by filtration and washing with water (deionized water). Thereafter, the ion-exchanged ZSM-5 was dried at 150° C. for 10 hours and then sintered at 500° C. for 3 hours. The resulting Pd-containing ZSM-5 was analyzed to contain Pd at a content of 0.25% by weight based on the weight of ZSM-5, as measured by ICP.

A catalyst body was prepared in the same manner as in Comparative Example 2, with the exception of using Pd (0.25)-containing ZSM-5 instead of hydrogen type ZSM-5mordenite.

The catalyst body thus obtained was pre-treated and used for disproportionation/transalkylation in the same manner as in Comparative Example 2. The reaction results are summarized in Table 2, below.

TABLE 2

| | Ex. 1 | Ex. 2 | Ex. 3 | Ex. 4 | Ex. 5 | Ex. 6 |
|---|---|---|---|---|---|---|
| Rxn. Condition | Temp.: 350° C., Press.: 30 kg/cm$^2$, WHSV = 3.5 hr$^{-1}$, H$_2$/HC (Molar ratio):3 | | | | | |
| EB in XYL (%) | 0.30 | 0.37 | 1.00 | 0.35 | 0.35 | 0.31 |
| XYL Yield (%) | 36.90 | 36.18 | 35.10 | 36.20 | 36.22 | 35.10 |
| Bz Purity (%) | 99.88 | 99.81 | 99.76 | 99.80 | 99.90 | 98.08 |
| Conversion Rate (%) | 45.61 | 45.34 | 44.21 | 45.39 | 45.07 | 45.87 |

As is understood from data of Tables 1 and 2, the content of ethylbenzene in C8 aromatics was remarkably decreased in Examples 1 to 6 using Pd-exchanged (Pd-ion-exchanged) ZSM-5 (Pd-ZSM-5), compared to Comparative Examples 1 to 4 using H-ZSM-5.

Particularly, Comparative Example 4 using Pd-exchanged mordenite (MOR) did not exhibit greatly reduced content of ethylbenzene in C8 aromatics, compared to Comparative Example 2 using H-MOR. In contrast, C8 aromatics produced in Examples 2 and 4 using Pd-exchanged ZSM-5 (Pd-ZSM-5) were found to have dramatically reduced contents of ethylbenzene.

Moreover, no great reduction in ethylbenzene content of C8 aromatics was detected in Example 4 using both Pd-exchanged MOR and Pd-exchanged ZSM-5, compared to Example 2. As such, ion exchange of ZSM-5 with Pd was understood to have a significant effect on ethylbenzene reduction.

Meanwhile, it might be expected that the more is the ion exchange with Pd, the more advantageous the reduction of ethylbenzene is. However, in Example 6 using 0.25% by weight of Pd-loading, it was detected that the content of ethylbenzene was reduced, but the purity of benzene, which was produced together with xylene, was relatively low.

As described above, the catalysts using Pd-exchanged ZSM-5 as in the Examples could remarkably reduce the content of ethylbenzene in mixed xylene, with equal or higher mixed xylene yield compared to conventional catalysts using HZSM-5. In addition, catalysts using Pd-exchanged ZSM-5 brought about a great reduction in ethylbenzene content, compared to using Pd-exchanged MOR.

As described hitherto, the catalyst according to an embodiment of the present disclosure has an advantage over conventional catalysts because mixed xylene can be produced at high yield from a feedstock containing alkyl aromatic compounds through disproportionation/transalkylation/dealkylation while the content of ethylbenzene in the product C8 aromatic hydrocarbons can be reduced. As a result, the efficiency of the subsequent para-xylene separation process can be improved, with the reduction of overall process costs. Therefore, the catalyst of the present disclosure is expected to find broad commercial applications in the future.

Accordingly, it should be understood that simple modifications and variations of the present disclosure may be easily used by those skilled in the art, and such modifications or variations may fall within the scope of the present disclosure.

What is claimed is:

1. A method for preparing C8 aromatics, the method comprising the steps of:
providing a feedstock containing benzene, toluene, and/or C9+ aromatics; and
subjecting the feedstock to at least one reaction selected from disproportionation, transalkylation, and dealkylation in the presence of a catalyst to give a product having an increased amount of C8 aromatic hydrocarbons,
wherein the catalyst comprises,
(A) a mixed support comprising (i) an MFI-type first zeolite having a silica-alumina molar ratio (SAR) of 10 to 200 and containing a reduced form of palladium (Pd) within the pores and/or crystalline structure thereof through ion-exchange, and (ii) a second zeolite having a silica-alumina molar ratio of 10 to 200 and a pore size of 6 to 9 Å; and (B) at least one first metal supported onto the mixed support and selected from the group consisting of platinum (Pt), rhenium (Re), and molybdenum (Mo), in which the first metal is used in an amount of 0.01 to 5% by weight, based on the total weight of the catalyst, and
wherein the C8 aromatic hydrocarbons contain ethylbenzene at a content of less than 1.5% by weight.

2. The method of claim 1, wherein the first zeolite contains palladium at a content of 0.001 to 0.25% by weight, based on the weight thereof.

3. The method of claim 1, wherein the MFI-type zeolite is ZSM-5.

4. The method of claim 1, wherein the first metal is in a reduced form, a partially oxidized form, or a sulfide form.

5. The method of claim 4, wherein the first metal is platinum and is in a sulfide form.

6. The method of claim 4, wherein the first metal is rhenium and is in a reduced form or a sulfide form.

7. The method of claim 4, wherein the first metal is molybdenum and is in a partially oxide form or a sulfide form.

8. The method of claim 1, the catalyst further comprises a second metal selected from the group consisting of tin (Sn), lead (Pb), and a combination thereof, wherein the second metal is used in an amount of 0.01 to 5% by weight, based on the total weight of the catalyst.

9. The method of claim 8, wherein the first metal is platinum, and the second metal is at least one selected from the group consisting of tin (Sn) and lead (Pb), with the atom ratio of the first metal to the second metal ranging 1:0.5 to 50.

10. The method of claim 1, wherein the second zeolite is mordenite, beta-zeolite, or a combination thereof.

11. The method of claim 1, wherein a mixing ratio of the first zeolite and the second zeolite in the mixed support is in a range of 1:1 to 9, based on the weight thereof.

12. The method of claim 1, wherein the mixed support is shaped with an inorganic binder and comprises: (i) 5 to 70% by weight of the first zeolite, (ii) 10 to 90% by weight of the second zeolite, and (iii) 1 to 70% by weight of the inorganic binder, based on the weight thereof.

13. The method of claim 12, wherein the inorganic binder is at least one selected from the group consisting of alumina, silica, silica-alumina, bentonite, kaolin, clinoptilolite, and montmorillonite.

14. The method of claim 1, wherein the feedstock containing alkyl aromatics is derived from at least one of: catalytic reformation of naphtha; thermal cracking of naphtha, distillates, or other hydrocarbons for production of light olefins and aromatic-rich fractions; and catalytic or thermal cracking of heavy oil fractions for production of hydrocarbons having a gasoline boiling point range.

15. The method of claim 1, wherein at least one reaction from disproportionation, transalkylation and dealkylation is carried out in the condition of a reaction temperature of 200 to 600° C., a reaction pressure of 5 to 100 kgf/cm$^2$, a hydrogen/hydrocarbon molar ratio of 0.1 to 20, and a space velocity (WHSV) of 0.1 to 20 hr$^{-1}$.

* * * * *